(12) United States Patent
Wilkinson et al.

(10) Patent No.: US 6,915,662 B2
(45) Date of Patent: *Jul. 12, 2005

(54) HYDROCARBON GAS PROCESSING

(75) Inventors: John D. Wilkinson, Midland, TX (US); Hank M. Hudson, Midland, TX (US); Michael C. Pierce, Odessa, TX (US)

(73) Assignee: ElkCorp., Dallas, TX (US)

( * ) Notice: Subject to any disclaimer, the term of this patent is extended or adjusted under 35 U.S.C. 154(b) by 613 days.

This patent is subject to a terminal disclaimer.

(21) Appl. No.: 10/003,453

(22) Filed: Oct. 26, 2001

(65) Prior Publication Data

US 2002/0065446 A1 May 30, 2002

Related U.S. Application Data

(63) Continuation of application No. 09/677,220, filed on Oct. 2, 2000.

(51) Int. Cl.$^7$ .................................................. F25J 3/02
(52) U.S. Cl. .......................................... 62/621; 62/625
(58) Field of Search ............................................ 62/621

(56) References Cited

U.S. PATENT DOCUMENTS

| | | | |
|---|---|---|---|
| 3,292,380 A | 12/1966 | Bucklin | 62/20 |
| 4,140,504 A | 2/1979 | Campbell et al. | 62/621 |
| 4,157,904 A | 6/1979 | Campbell et al. | 62/27 |

(Continued)

FOREIGN PATENT DOCUMENTS

| | | |
|---|---|---|
| EP | 1114808 | 7/2001 |
| WO | 99/23428 | 5/1999 |
| WO | 99/37962 | 7/1999 |
| WO | 00/33006 | 6/2000 |

OTHER PUBLICATIONS

Mowrey, E. Ross, "Efficient, High Recovery of Liquids from Natural Gas Utilizing a High Pressure Absorber", Proceedings of the Eighty–First Annual Convention of the Gas Processors Association, Dallas, Texas, Mar. 11–13, 2002.

*Primary Examiner*—Ellen M McAvoy
(74) *Attorney, Agent, or Firm*—Fitzpatrick, Cella, Harper & Scinto

(57) ABSTRACT

A process for the recovery of ethane, ethylene, propane, propylene and heavier hydrocarbon components from a hydrocarbon gas stream is disclosed. In recent years, the preferred method of separating a hydrocarbon gas stream generally includes supplying at least portions of the gas stream to a fractionation tower having at least one reboiler, and often one or more side reboilers, to supply heat to the column by withdrawing and heating some of the tower liquids to produce stripping vapors that separate the more volatile components from the desired components. The reboiler and side reboilers (if any) are typically integrated into the feed stream cooling scheme to provide at least a portion of the refrigeration needed to condense the desired components for subsequent fractionation in the distillation column. In the process disclosed, the tower reboiling scheme is modified to use one or more tower liquid distillation streams from a point higher in the column than is used in the conventional reboiling scheme, providing colder stream(s) for the reboiler(s) that allow more effective cooling of the feed streams and thereby improve the efficiency with which the desired components are recovered. In addition, the tower liquid streams withdrawn from a higher point in the column contain larger quantities of the more volatile components, which when vaporized provide better stripping of undesirable components like carbon dioxide without reducing the recovery of the desired components. The heated distillation stream is returned to a lower point on the fractionation tower that is separated from the withdrawal point by at least one theoretical stage.

13 Claims, 9 Drawing Sheets

U.S. PATENT DOCUMENTS

| | | | |
|---|---|---|---|
| 4,171,964 A | 10/1979 | Campbell et al. | 62/24 |
| 4,185,978 A | 1/1980 | McGalliard et al. | 62/28 |
| 4,251,249 A | 2/1981 | Gulsby | 62/28 |
| 4,278,457 A | 7/1981 | Campbell et al. | 62/24 |
| 4,519,824 A | 5/1985 | Huebel | 62/26 |
| 4,617,039 A | 10/1986 | Buck | 62/26 |
| 4,687,499 A | 8/1987 | Aghili | 62/24 |
| 4,689,063 A | 8/1987 | Paradowski et al. | 62/28 |
| 4,690,702 A | 9/1987 | Paradowski et al. | 62/23 |
| 4,710,214 A | 12/1987 | Sharma et al. | 62/621 |
| 4,851,020 A | 7/1989 | Montgomery, IV | 62/24 |
| 4,854,955 A | 8/1989 | Campbell et al. | 62/24 |
| 4,869,740 A | 9/1989 | Campbell et al. | 62/24 |
| 4,889,545 A | 12/1989 | Campbell et al. | 62/24 |
| 4,895,584 A | 1/1990 | Buck et al. | 62/621 |
| RE33,408 E | 10/1990 | Khan et al. | 62/29 |
| 5,114,451 A | 5/1992 | Rambo et al. | 62/623 |
| 5,275,005 A | 1/1994 | Campbell et al. | 62/24 |
| 5,555,748 A | 9/1996 | Campbell et al. | 62/621 |
| 5,566,554 A | 10/1996 | Vijayaraghavan et al. | 62/621 |
| 5,568,737 A | 10/1996 | Campbell et al. | 62/621 |
| 5,755,115 A | 5/1998 | Manley | 62/620 |
| 5,771,712 A | 6/1998 | Campbell et al. | 62/621 |
| 5,799,507 A | 9/1998 | Wilkinson et al. | 62/621 |
| 5,881,569 A | 3/1999 | Campbell et al. | 62/621 |
| 5,890,377 A | 4/1999 | Foglietta | 62/621 |
| 5,890,378 A | 4/1999 | Rambo et al. | 62/621 |
| 5,983,664 A | 11/1999 | Campbell et al. | 62/621 |
| 6,182,469 B1 | 2/2001 | Campbell et al. | 62/621 |
| 6,237,365 B1 | 5/2001 | Trebble | 62/621 |
| 2003/0158458 A1 | 8/2003 | Prim | 585/800 |

HYDROCARBON GAS PROCESSING

CROSS REFERENCE TO RELATED APPLICATIONS

This application is a continuation application under 37 C. F. R. 1.53(b) of application Ser. No. 09/677,220 filed Oct. 2, 2000.

BACKGROUND OF THE INVENTION

This invention relates to a process for the separation of a gas containing hydrocarbons.

Ethylene, ethane, propylene, propane and/or heavier hydrocarbons can be recovered from a variety of gases, such as natural gas, refinery gas, and synthetic gas streams obtained from other hydrocarbon materials such as coal, crude oil, naphtha, oil shale, tar sands, and lignite. Natural gas usually has a major proportion of methane and ethane, i.e., methane and ethane together comprise at least 50 mole percent of the gas. The gas also contains relatively lesser amounts of heavier hydrocarbons such as propane, butanes, pentanes and the like, as well as hydrogen, nitrogen, carbon dioxide and other gases.

The present invention is generally concerned with the recovery of ethylene, ethane, propylene, propane and heavier hydrocarbons from such gas streams. A typical analysis of a gas stream to be processed in accordance with this invention would be, in approximate mole percent, 88.41% methane, 6.65% ethane and other $C_2$ components, 2.26% propane and other $C_3$ components, 0.36% iso-butane, 0.45% normal butane, 0.31% pentanes plus, with the balance made up of nitrogen and carbon dioxide. Sulfur containing gases are also sometimes present.

The historically cyclic fluctuations in the prices of both natural gas and its natural gas liquid (NGL) constituents have at times reduced the incremental value of ethane, ethylene, propane, propylene, and heavier components as liquid products. Competition for processing rights has forced plant operators to maximize the processing capacity and recovery efficiency of their existing gas processing plants. Available processes for separating these materials include those based upon cooling and refrigeration of gas, oil absorption, and refrigerated oil absorption. Additionally, cryogenic processes have become popular because of the availability of economical equipment that produces power while simultaneously expanding and extracting heat from the gas being processed. Depending upon the pressure of the gas source, the richness (ethane, ethylene, and heavier hydrocarbons content) of the gas, and the desired end products, each of these processes or a combination thereof may be employed.

The cryogenic expansion process is now generally preferred for natural gas liquids recovery because it provides maximum simplicity with ease of start up, operating flexibility, good efficiency, safety, and good reliability. U.S. Pat. Nos. 3,292,380; 4,157,904; 4,171,964; 4,185,978; 4,251,249; 4,278,457; 4,519,824; 4,617,039; 4,687,499; 4,689,063; 4,690,702; 4,854,955; 4,869,740; 4,889,545; 5,275,005; 5,555,748; 5,568,737; 5,771,712; 5,799,507; 5,881,569; 5,890,378; 5,983,664; reissue U.S. Pat. No. 33,408; and co-pending application Ser. No. 09/439,508 describe relevant processes (although the description of the present invention in some cases is based on different processing conditions than those described in the cited U.S. patents and patent applications).

In a typical cryogenic expansion recovery process, a feed gas stream under pressure is cooled by heat exchange with other streams of the process and/or external sources of refrigeration such as a propane compression-refrigeration system. As the gas is cooled, liquids may be condensed and collected in one or more separators as high-pressure liquids containing some of the desired $C_2$+ components. Depending on the richness of the gas and the amount of liquids formed, the high-pressure liquids may be expanded to a lower pressure and fractionated. The vaporization occurring during expansion of the liquids results in further cooling of the stream. Under some conditions, pre-cooling the high pressure liquids prior to the expansion may be desirable in order to further lower the temperature resulting from the expansion. The expanded stream, comprising a mixture of liquid and vapor, is fractionated in a distillation (demethanizer) column. In the column, the expansion cooled stream(s) is (are) distilled to separate residual methane, nitrogen, and other volatile gases as overhead vapor from the desired $C_2$ components, $C_3$ components, and heavier hydrocarbon components as bottom liquid product.

If the feed gas is not totally condensed (typically it is not), at least a portion of the vapor remaining from the partial condensation can be passed through a work expansion machine or engine, or an expansion valve, to a lower pressure at which additional liquids are condensed as a result of further cooling of the stream. The pressure after expansion is essentially the same as the pressure at which the distillation column is operated. The combined vapor-liquid phases resulting from the expansion are supplied as a feed to the column. In recent years, the preferred processes for hydrocarbon separation involve feeding this expanded vapor-liquid stream at a mid-column feed point, with an upper absorber section providing additional rectification of the vapor phase. There are, however, processes wherein this expanded vapor-liquid stream is used as the top column feed. Typically, the vapor portion of the expanded stream and the demethanizer overhead vapor combine in an upper separator section in the fractionation tower as residual methane product gas. Alternatively, the cooled and expanded stream may be supplied to a separator to provide vapor and liquid streams, so that thereafter the vapor is combined with the tower overhead and the liquid is supplied to the column as a top column feed.

For those processes that include an upper rectification section, a reflux stream must be provided for the section. One manner for accomplishing this is to withdraw a vapor distillation stream from the upper section of the demethanizer tower, cool it to partially condense it by heat exchange with other process streams, e.g., part of the feed gas that has been cooled to substantial condensation and then expanded to cool it further. The liquid condensed from the vapor distillation stream is then supplied as the top feed to the demethanizer.

The purpose of this process is to perform a separation that produces a residue gas leaving the process which contains substantially all of the methane in the feed gas with essentially none of the $C_2$ components and heavier hydrocarbon components, and a bottoms fraction leaving the demethanizer which contains substantially all of the $C_2$ components and heavier hydrocarbon components with essentially no methane or more volatile components while meeting plant specifications for maximum permissible carbon dioxide content. The present invention provides a means for providing a new plant or modifying an existing processing plant to achieve this separation at significantly lower capital cost by reducing the size of or eliminating the need for a product treating system for removal of carbon dioxide. Alternatively, the present invention, whether applied in a new facility or as a modification to an existing processing plant, can be used to recover more $C_2$ components and heavier hydrocarbon components in the bottom liquid product for a given carbon dioxide concentration in the feed gas than other processing schemes.

In accordance with the present invention, it has been found that $C_2$ recoveries in excess of 66 percent can be maintained while maintaining the carbon dioxide content of the bottom liquid product within specifications and providing essentially complete rejection of methane to the residue gas stream. The present invention, although applicable at lower pressures and warmer temperatures, is particularly advantageous when processing feed gases at pressures in the range of 600 to 1000 psia or higher under conditions requiring column overhead temperatures of −120° F. or colder.

The present invention uses a modified reboiler scheme which can be applied to any type of NGL recovery system. In a typical reboiler or side reboiler application in a distillation column, the entire column down-flowing liquid stream is withdrawn from the tower and passed through a heat exchanger, then returned to the column at essentially the same point in the column. In this modified reboiler system, a portion of the column down-flowing liquid is withdrawn from a point higher in the column, i.e., separated from the return point by at least one theoretical stage. Even though the flow rate of the liquid may be lower, it is usually much colder and can have advantages in improving recovery or reducing exchanger size.

It has been found that when the present invention is applied to prior art processes for NGL recovery, the recovery of $C_2$ components and heavier components is improved by one to two percent. The improvement in recovery is much greater, however, when it is desirable to reduce the carbon dioxide content in the recovered NGL product. Recovery of ethane in a typical NGL recovery plant also results in recovery of at least some of the carbon dioxide contained in the feed gas because carbon dioxide falls in between methane and ethane in relative volatility. Therefore, as ethane recovery increases, so does the recovery of carbon dioxide in the NGL product. By applying the modified reboiler scheme of the present invention, the applicants have found that it is possible to significantly improve recovery of ethane in the NGL product compared to use of the conventional reboiler or side reboiler systems when the column is reboiled to meet the desired carbon dioxide content in the NGL product.

For a better understanding of the present invention, reference is made to the following examples and drawings. Referring to the drawings.

In the following explanation of the above figures, tables are provided summarizing flow rates calculated for representative process conditions. In the tables appearing herein, the values for flow rates (in pound moles per hour) have been rounded to the nearest whole number for convenience. The total stream rates shown in the tables include all non-hydrocarbon components and hence are generally larger than the sum of the stream flow rates for the hydrocarbon components. Temperatures indicated are approximate values rounded to the nearest degree. It should also be noted that the process design calculations performed for the purpose of comparing the processes depicted in the figures are based on the assumption of no heat leak from (or to) the surroundings to (or from) the process. The quality of commercially available insulating materials makes this a very reasonable assumption and one that is typically made by those skilled in the art.

DESCRIPTION OF THE PRIOR ART

Figure 1:
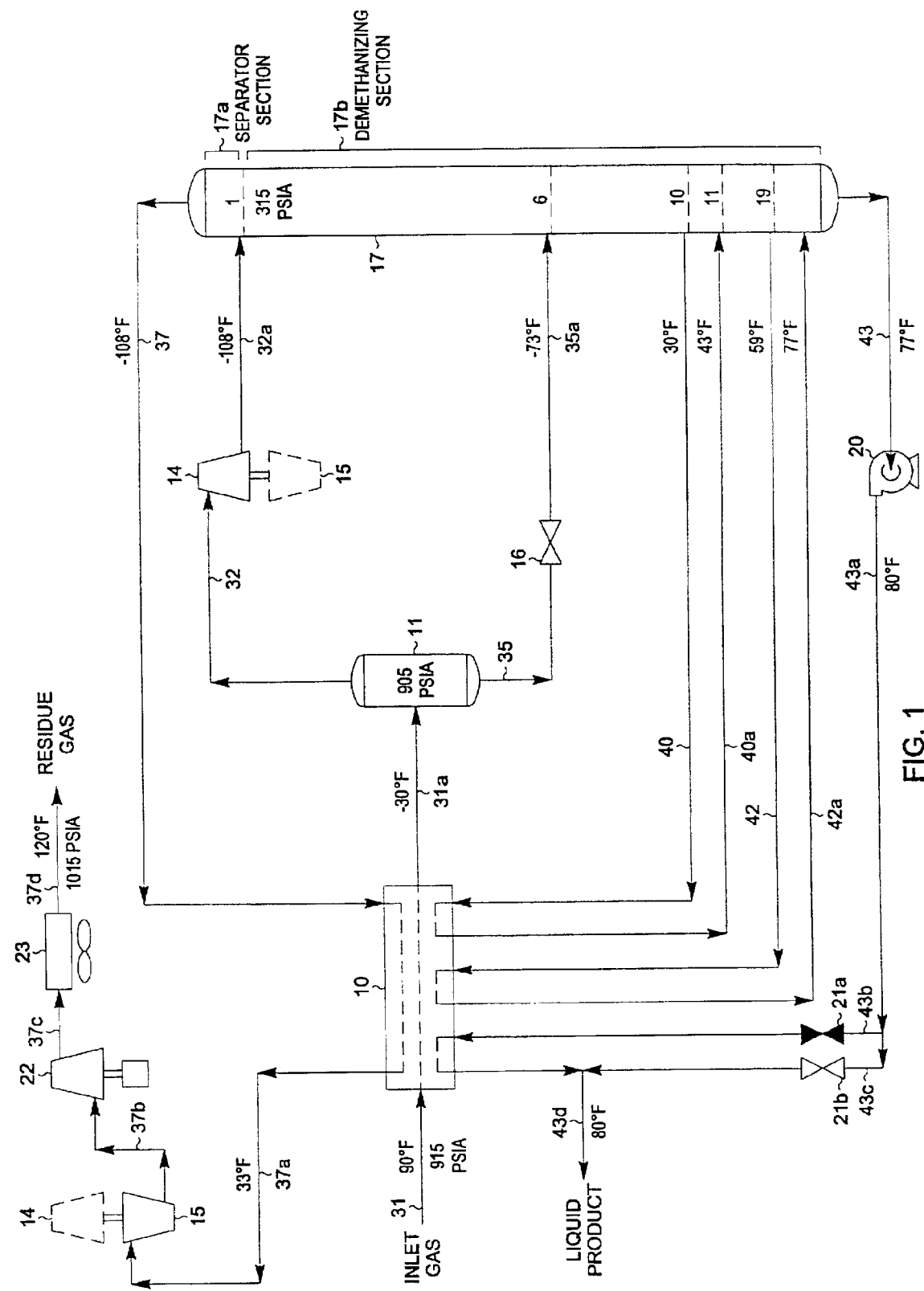
FIG. 1 is a flow diagram of a prior art cryogenic natural gas processing plant.

FIG. 1 is a process flow diagram showing the design of a processing plant to recover $C_2+$ components from natural gas using prior art according to U.S. Pat. No. 3,292,380. In this simulation of the process, inlet gas enters the plant at 90° F. and 915 psia as stream 31. If the inlet gas contains a concentration of sulfur compounds which would prevent the product streams from meeting specifications, the sulfur compounds are removed by appropriate pretreatment of the feed gas (not illustrated). In addition, the feed stream is usually dehydrated to prevent hydrate (ice) formation under cryogenic conditions. Solid desiccant has typically been used for this purpose.

The feed stream 31 is cooled in exchanger 10 by heat exchange with cold residue gas at −108° F. (stream 37), demethanizer reboiler liquids at 59° F. (stream 42), and demethanizer side reboiler liquids at 30° F. (stream 40). Note that in all cases exchanger 10 is representative of either a multitude of individual heat exchangers or a single multi-pass heat exchanger, or any combination thereof. (The decision as to whether to use more than one heat exchanger for the indicated cooling services will depend on a number of factors including, but not limited to, inlet gas flow rate, heat exchanger size, stream temperatures, etc.) Note also that heat exchanger 10 was intended to use demethanizer liquid product (stream 43a) to provide a portion of the feed gas cooling, but as will be explained later this stream is too warm to be used for this purpose. The cooled stream 31a enters separator 11 at −30° F. and 905 psia where the vapor (stream 32) is separated from the condensed liquid (stream 35).

The vapor (stream 32) from separator 11 enters a work expansion machine 14 in which mechanical energy is extracted from this portion of the high pressure feed. The machine 14 expands the vapor substantially isentropically from a pressure of about 905 psia to the operating pressure (approximately 315 psia) of demethanizer column 17, with the work expansion cooling the expanded stream 32a to a temperature of approximately −108° F. The typical commercially available expanders are capable of recovering on the order of 80–85% of the work theoretically available in an ideal isentropic expansion. The work recovered is often used to drive a centrifugal compressor (such as item 15), that can be used to re-compress the residue gas (stream 37a), for example. The expanded and partially condensed stream 32a is supplied to separator section 17a in the upper region of demethanizer tower 17. The liquids separated therein become the top feed to theoretical stage 1 in demethanizing section 17b.

The liquid (stream 35) from separator 11 is flash expanded through an appropriate expansion device, such as expansion valve 16, to the operating pressure of demethanizer tower 17. During expansion a portion of the stream is vaporized, resulting in cooling of the total stream. In the process illustrated in FIG. 1, the expanded stream 35a leaving expansion valve 16 reaches a temperature of −73° F. and is supplied to a mid-column feed point on demethanizer tower 17.

The demethanizer 17 is a conventional distillation column containing a plurality of vertically spaced trays, one or more packed beds, or some combination of trays and packing. As is often the case in natural gas processing plants, the demethanizer tower may consist of two sections. The upper section 17a is a separator wherein the partially condensed top feed is divided into its respective vapor and liquid portions, and wherein the vapor rising from the lower distillation or demethanizing section 17b is combined with the vapor portion of the top feed to form the cold residue gas distillation stream 37 which exits the top of the tower. The lower, demethanizing section 17b contains the trays and/or packing and provide the necessary contact between the liquids falling downward and the vapors rising upward. The demethanizer column 17 also includes reboilers which heat and vaporize portions of the liquids flowing down the column to provide the stripping vapors which flow up the column.

In many case, the temperature of the liquid product (stream 43) exiting the bottom of the tower is controlled on the basis of maintaining the desired ratio of methane to ethane in the liquid product. A typical specification for this is a methane to ethane ratio of 0.025:1 on a molar basis in the bottom product. In this case, however, the concentration of carbon dioxide in the liquid product would exceed the plant owner's specification for a carbon dioxide to ethane ratio of 0.05:1 on a molar basis if the demethanizer was controlled to maintain this methane:ethane ratio. Thus, if operated in this manner this plant design would require the addition of a treating system to remove carbon dioxide from the hydrocarbons in order to produce a marketable liquid product. There are many options for removing the carbon dioxide (treating the incoming feed gas, treating the total liquid product, treating the ethane product after fractionation, etc.), but all of these options will add not only to the capital cost of the plant (due to the cost of installing the treating system) but also to the operating expense of the plant (due to energy and chemical consumption in the treating system).

One way to keep the ethane product within the carbon dioxide specification is to operate the demethanizer in a manner to strip the carbon dioxide from the bottom liquid product, by adding more reboil heat to the column using the side reboiler and/or the bottom reboiler as illustrated here for the FIG. 1 process. This results in the liquid product (stream 43) exiting the bottom of the tower at 77° F., whereupon it is pumped to approximately 480 psia (stream 43a) in pump 20. (The discharge pressure of the pump is usually set by the ultimate destination of the liquid product. Generally the liquid product flows to storage after being used for heat exchange and the pump discharge pressure is set so as to prevent any vaporization of stream 43a as it warms to ambient temperature.) Because stream 43a is so warm, however, it cannot be used for feed gas cooling in heat exchanger 10. Accordingly, block valve 21a must be closed and block valve 21b opened to bypass the stream around heat exchanger 10 and send it directly to storage (stream 43d).

The residue gas (stream 37) passes countercurrently to the incoming feed gas in heat exchanger 10 where it is heated to 33° F. (stream 37a). The residue gas is then re-compressed in two stages. The first stage is compressor 15 driven by expansion machine 14, and the second stage is compressor 22 driven by a supplemental power source. After stream 37c is cooled to 120° F. by cooler 23, the residue gas product (stream 37d) flows to the sales pipeline at 1015 psia, sufficient to meet line requirements (usually on the order of the inlet pressure).

A summary of stream flow rates and energy consumption for the process illustrated in FIG. 1 is set forth in the following table:

TABLE I (FIG. 1)
Stream Flow Summary - (Lb. Moles/Hr)

| Stream | Methane | Ethane | Propane | Butanes+ | C. Dioxide | Total |
|---|---|---|---|---|---|---|
| 31 | 25338 | 1905 | 647 | 320 | 307 | 28659 |
| 32 | 24929 | 1777 | 534 | 181 | 296 | 27860 |
| 35 | 409 | 128 | 113 | 139 | 11 | 799 |
| 40 | 14 | 1900 | 730 | 342 | 531 | 3517 |
| 37 | 25338 | 1129 | 94 | 6 | 268 | 26977 |
| 43 | 0 | 776 | 553 | 314 | 39 | 1682 |

Recoveries*

| | |
|---|---|
| Ethane | 40.74% |
| Propane | 85.47% |
| Butanes+ | 98.09% |

Horsepower

| | |
|---|---|
| Residue Compression | 13,296 |

*(Based on un-rounded flow rates)

The carbon dioxide:ethane ratio in the bottom liquid product for the FIG. 1 process is 0.05:1, complying with the plant owner's specification. Note, however, that the methane:ethane ratio in the bottom product is 0.000003:1 on a molar basis, versus the allowable ratio of 0.025:1, indicating the degree of over-stripping required to control the carbon dioxide content of the liquid product at the required level. Examination of the recovery levels displayed in Table I shows that operating the FIG. 1 process in this manner to reduce the carbon dioxide content in the ethane product causes a substantial reduction in liquids recovery. When operated at a methane:ethane ratio of 0.025:1 in the bottom product, calculations indicate that the FIG. 1 process can achieve an ethane recovery of 69.64%, a propane recovery of 96.18%, and a butanes+ recovery of 99.66%. Unfortunately, the resulting carbon dioxide:ethane ratio (0.087:1) is too high to meet the plant owner's specification when the plant is operated in this manner. Thus, the requirement to operate the FIG. 1 process to reduce the concentration of carbon dioxide in the liquid product causes reductions in the ethane, propane, and butanes+ recoveries of over 28 percentage points, 10 percentage points, and 1 percentage point, respectively, for the prior art process.

There are two factors at work in the FIG. 1 process that result in less liquids recovery from the bottom of demethanizer tower 17 when the tower is operated to control the carbon dioxide content of the liquid product. First, when the temperature at the bottom of demethanizer column 17 is raised to 77° F. by reboiling the column more, the temperatures at each point in the column increase. This reduces the amount of cooling that the tower liquid streams (streams 40, 42, and 43) can supply to the feed gas in heat exchanger 10. As a result, the cooled feed stream (stream 31a) entering separator 11 is warmer, which in turn results in the lower ethane retention in demethanizer column 17. Second, the higher temperatures in the lower section of demethanizer column 17 cause the temperatures in the upper section to be higher also, resulting in less methane liquid entering the lower section of demethanizer column 19. When this liquid methane is subsequently vaporized by the side reboiler and main reboiler attached to demethanizer column 17, the methane vapor helps to strip the carbon dioxide from the liquids flowing down the column. With less methane available in the FIG. 1 process to strip the carbon dioxide, more of the ethane in the liquids must be vaporized to serve as stripping gas. Since the relative volatilities for carbon dioxide and ethane are very similar, the ethane vapor is a much less effective stripping agent than the methane vapor, which reduces the stripping efficiency in the column and causes lower recovery.

DESCRIPTION OF THE INVENTION

EXAMPLE

Figure 2:
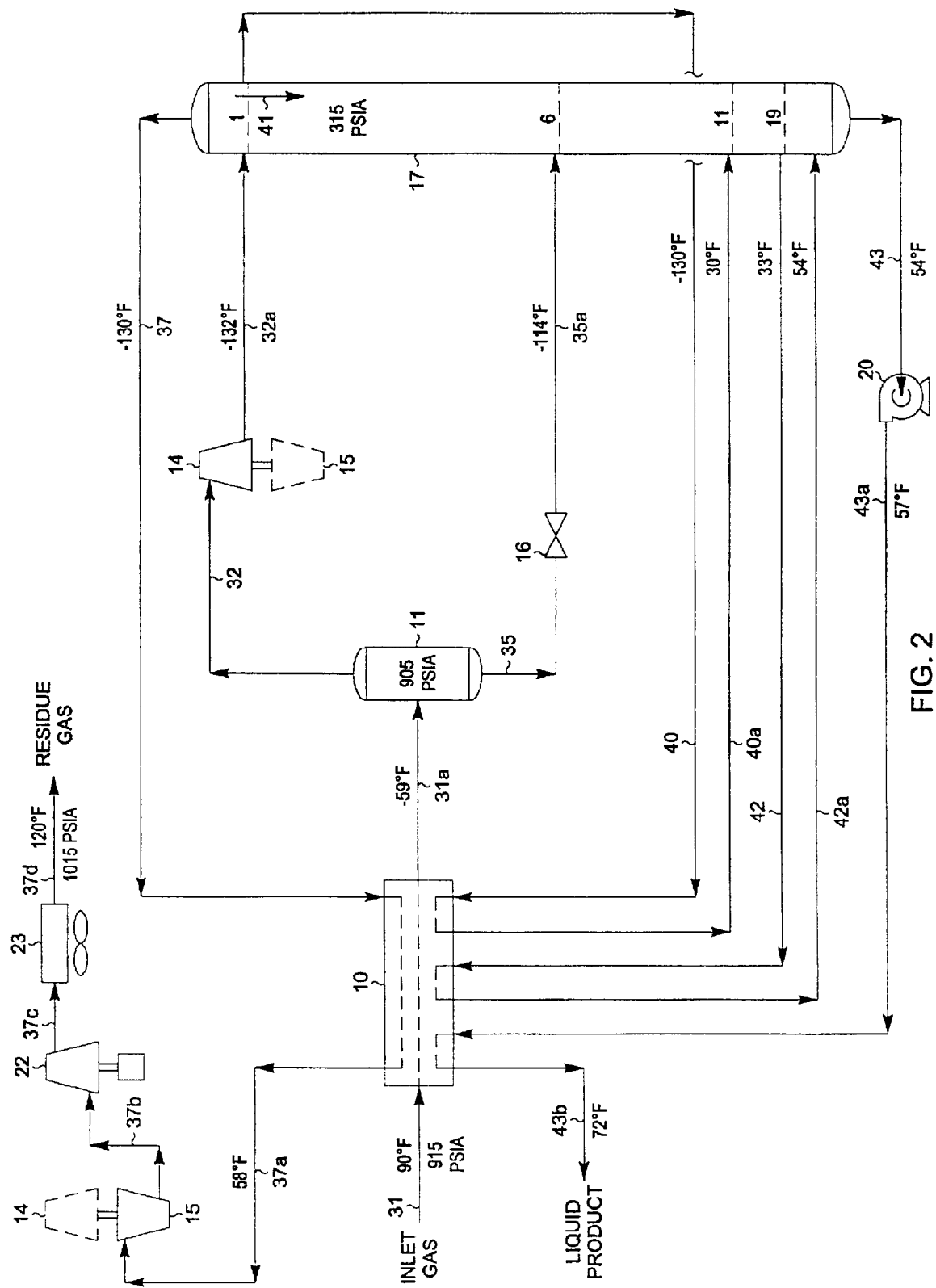
FIG. 2 is a flow diagram illustrating how the processing plant of FIG. 1 can be adapted to be a natural gas processing plant in accordance with the present invention.

FIG. 2 illustrates a flow diagram of a process in accordance with the present invention. The feed gas composition and conditions considered in the process presented in FIG. 2 are the same as those in FIG. 1. Accordingly, the FIG. 2 process can be compared with that of the FIG. 1 process to illustrate the advantages of the present invention.

In the simulation of the FIG. 2 process, inlet gas enters at 90° F. and a pressure of 915 psia as stream 31. The feed stream 31 is cooled in exchanger 10 by heat exchange with cold residue gas at −130° F. (stream 37), demethanizer liquid product at 57° F. (stream 43a), demethanizer reboiler liquids at 33° F. (stream 42), and a portion of the liquids from the upper section of demethanizer column 17 at −130° F. (stream 40). The cooled stream 31a enters separator 11 at −59° F. and 905 psia where the vapor (stream 32) is separated from the condensed liquid (stream 35).

The condensed liquid (stream 35) from separator 11 is flash expanded through an appropriate expansion device, such as expansion valve 16, to the operating pressure (approximately 315 psia) of demethanizer tower 17. During expansion a portion of the stream is vaporized, resulting in cooling of the total stream. In the process illustrated in FIG. 2, the expanded stream 35a leaving expansion valve 16 reaches a temperature of −114° F. and is supplied to demethanizer column 17 at a mid-column feed point.

The vapor (stream 32) from separator 11 enters a work expansion machine 14 in which mechanical energy is extracted from this portion of the high pressure feed. The machine 14 expands the vapor substantially isentropically from a pressure of about 905 psia to the operating pressure of demethanizer tower 17, with the work expansion cooling the expanded stream 32a to a temperature of approximately −132° F. The expanded and partially condensed stream 32a is thereafter supplied to demethanizer column 17 as the top column feed. The vapor portion of stream 32a combines with the vapors rising from the top fractionation stage of the column to form distillation stream 37, which is withdrawn from an upper region of the tower.

The liquid portion of stream 32a is used to contact the vapors rising from the lower fractionation stages of demethanizer column 17 and rectify the desired $C_2$ components and heavier components from the vapors, and is then divided into two portions. One portion (stream 41), containing about 40% of the total liquid, is directed onto the lower fractionation stages in demethanizer column 17 to further contact and rectify the vapors rising upward.

The other portion (stream 40), containing the remaining 60% of the liquid, is withdrawn from the tower and directed to heat exchanger 10 where it supplies part of the feed gas cooling as it is heated to 30° F. and partially vaporized. The heated stream 40a is thereafter supplied to demethanizer column 17 at a mid-column feed point, separated from the point where stream 40 was withdrawn from the column by at least one theoretical stage. In this case, the partially vaporized stream 40a flows to the same point on the column that was used for the side reboiler return (theoretical stage 11 in demethanizer tower 17) in the FIG. 1 process, which is the equivalent often theoretical stages lower than the liquid stream withdrawal point in the fractionation system (theoretical stage 1 in demethanizer tower 17).

The liquid product (stream 43) exits the bottom of demethanizer tower 17 at 54° F. This stream is pumped to approximately 480 psia (stream 43a) in pump 20 and then directed to heat exchanger 10 where it is heated to 72° F. as it supplies part of the feed gas cooling as described previously. The residue gas (stream 37) passes countercurrently to the incoming feed gas in heat exchanger 10 where it is heated to 58° F. (stream 37a). The residue gas is then re-compressed in two stages, compressor 15 driven by expansion machine 14 and compressor 22 driven by a supplemental power source. After stream 37c is cooled to 120° F. by cooler 23, the residue gas product (stream 37d) flows to the sales pipeline at 1015 psia.

A summary of stream flow rates and energy consumption for the process illustrated in FIG. 2 is set forth in the following table:

TABLE II (FIG. 2)
Stream Flow Summary - (Lb. Moles/Hr)

| Stream | Methane | Ethane | Propane | Butanes+ | C. Dioxide | Total |
|---|---|---|---|---|---|---|
| 31 | 25338 | 1905 | 647 | 320 | 307 | 28659 |
| 32 | 22905 | 1382 | 331 | 87 | 252 | 25094 |
| 35 | 2433 | 523 | 316 | 233 | 55 | 3565 |
| 40 | 1334 | 565 | 186 | 51 | 70 | 2208 |
| 37 | 25306 | 637 | 27 | 1 | 243 | 26356 |
| 43 | 32 | 1268 | 620 | 319 | 64 | 2303 |

| Recoveries* | |
|---|---|
| Ethane | 66.58% |
| Propane | 95.91% |
| Butanes+ | 99.63% |

| Horsepower | |
|---|---|
| Residue Compression | 15,400 |

*(Based on un-rounded flow rates)

Unlike the prior art process shown in FIG. 1, both the carbon dioxide:ethane ratio (0.05:1) and the methane:ethane ratio (0.025:1) in the bottom liquid product can be controlled at the specifications required by the client in the FIG. 2 process. Comparison of the recovery levels displayed in Tables I and II shows that the present invention allows achieving much higher liquids recovery efficiency than the FIG. 1 process when it is operated in a fashion to limit the carbon dioxide content of its liquid product. A comparison of Tables I and 11 shows that, compared to the prior art, the present invention improves ethane recovery from 40.74% to 66.58%, propane recovery from 85.47% to 95.91%, and butanes+ recovery from 98.09% to 99.63%. Comparison of Tables I and II further shows that the higher the product yields were not simply the result of increasing the horsepower (utility) requirements. To the contrary, when the present invention is employed as in this Example, not only do the ethane, propane, and butanes+ recoveries increase over those of the prior art process, liquid recovery efficiency also increases by 41 percent (in terms of ethane recovered per unit of horsepower expended). The FIG. 2 process recovers 0.83 gallons per hour of ethane per unit of horsepower consumed, versus 0.59 gallons per hour per unit of horsepower for the FIG. 1 process.

A significant benefit achieved by the present invention illustrated in FIG. 2 is that the modified reboiler scheme provides colder column liquids for use in refrigerating the incoming feed streams. This increases the cooling available to the inlet gas, as not only can considerably more duty be obtained from the liquid in this case, but at a colder temperature level. At the same time, more methane is introduced lower in demethanizer column 17 than would otherwise be there when reboiling the column to meet the carbon dioxide content. (Note that stream 40 in the FIG. 2 process contains 1334 Lb. Moles/Hr of methane, whereas stream 40 in the FIG. 1 process contains only 14 Lb. Moles/Hr of methane.) This additional methane provided by the present invention in the FIG. 2 process helps to strip the carbon dioxide from the liquids flowing downward in the stripping column. The quantity of carbon dioxide in the NGL product from the FIG. 2 process can be adjusted by appropriate control of the quantity of liquid withdrawn to feed the modified reboiler system instead of being directed to the fractionation stages in the upper section of demethanizer column 17.

OTHER EMBODIMENTS

Figure 3:
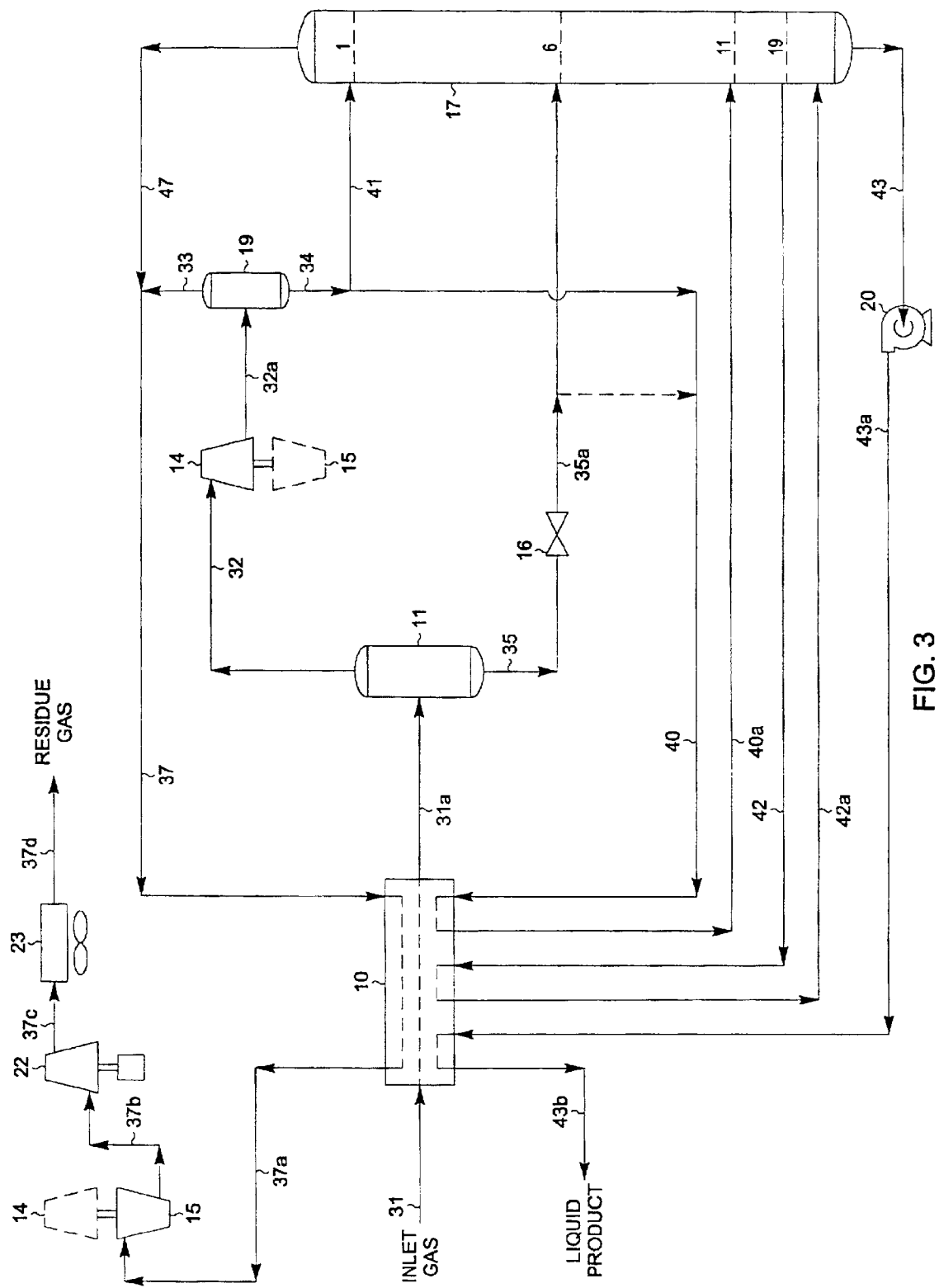
FIG. 3 is a flow diagram illustrating an alternative adaptation of FIG. 1 to be a natural gas processing plant in accordance with the present invention.
Figure 4:
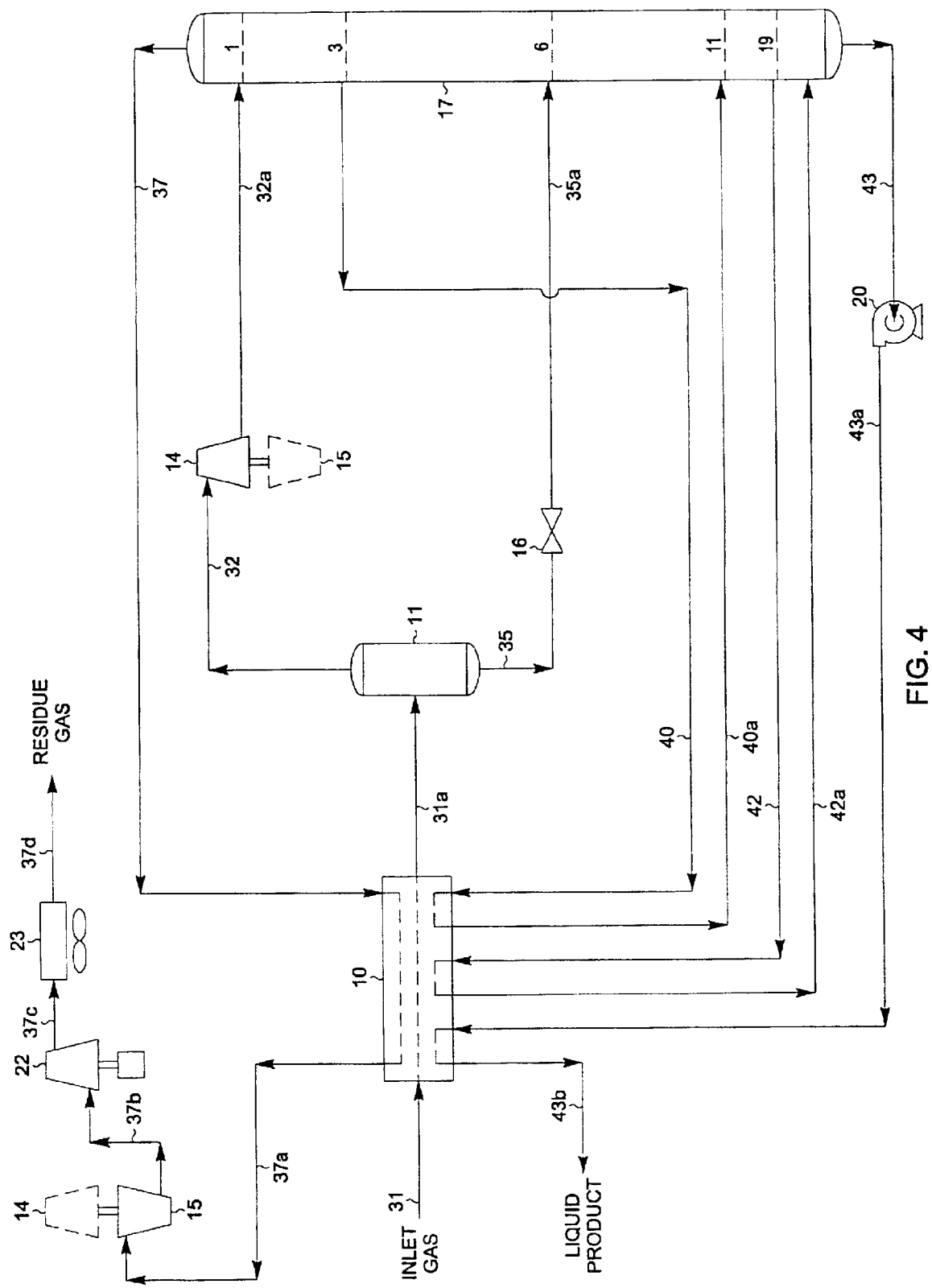
FIG. 4 is a flow diagram illustrating an alternative adaptation of FIG. 1 to be a natural gas processing plant in accordance with the present invention.
Figure 5:
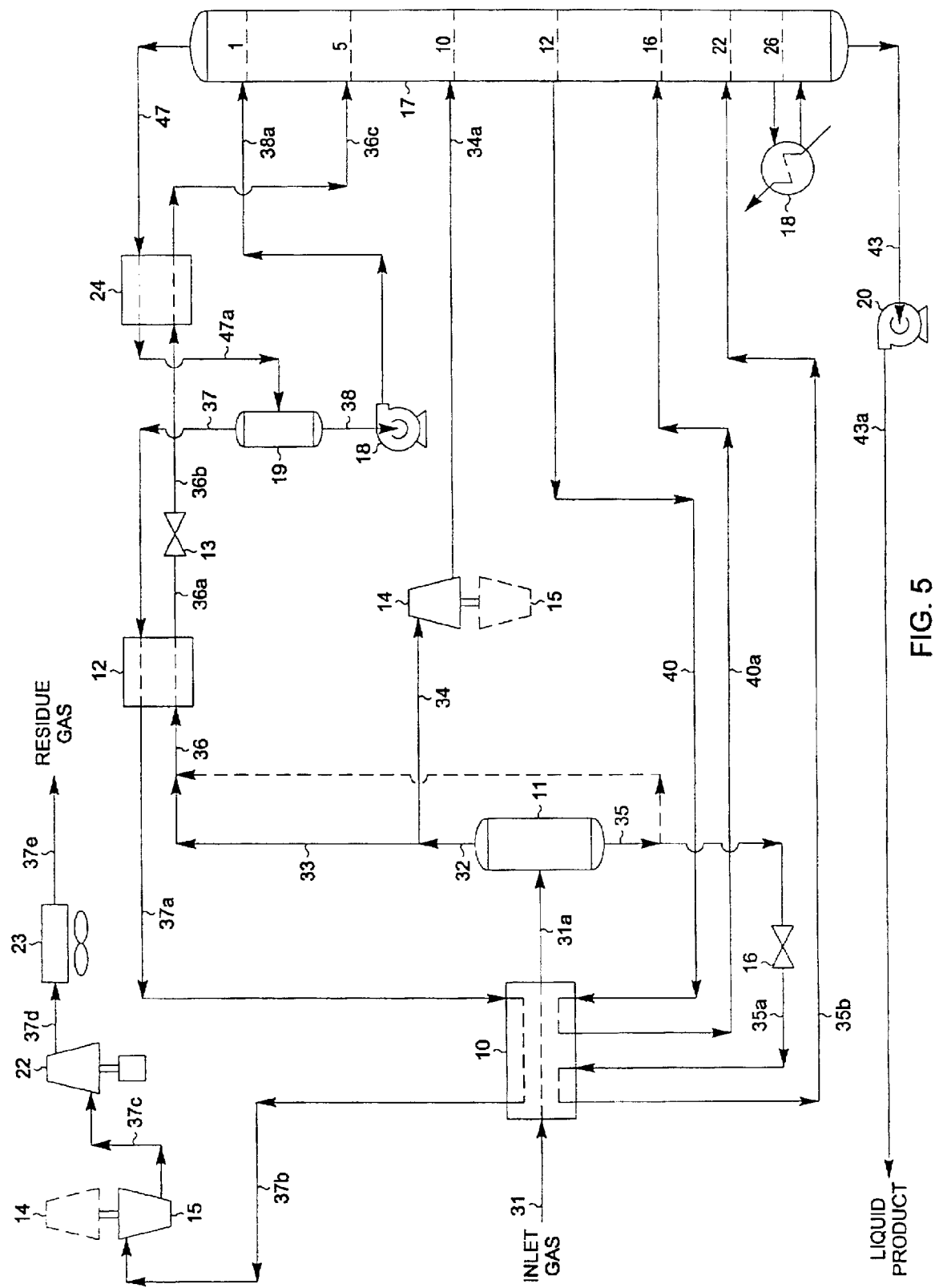
FIG. 5 is a flow diagram illustrating how an alternative prior art process can be adapted to be a natural gas processing plant in accordance with the present invention.

FIGS. 3 and 4 are flow diagrams illustrating alternative manners in which the process and apparatus described and depicted in U.S. Pat. No. 3,292,380 can be adapted to be natural gas processing plants in accordance with the present invention. It should be noted that in the FIG. 3 embodiment of the present invention, the distillation stream (stream 40) used for the modified reboiler scheme is produced by dividing the liquids formed in stream 32*a* during expansion (stream 34 from separator 19) external to demethanizer tower 17. This could also have been accomplished by routing all of the expanded stream (stream 32*a*) from work expansion machine 14 to a separator section in the upper part of demethanizer tower 17 to separate the liquids, then dividing the liquids to produce the reflux stream for the tower (stream 41) and the distillation stream for the modified reboiler scheme (stream 40). FIG. 5 is a flow diagram illustrating one manner in which the process and apparatus described and depicted in U.S. Pat. No. 4,854,955 can be adapted to be a natural gas processing plant in accordance with the present invention.

Figure 6:
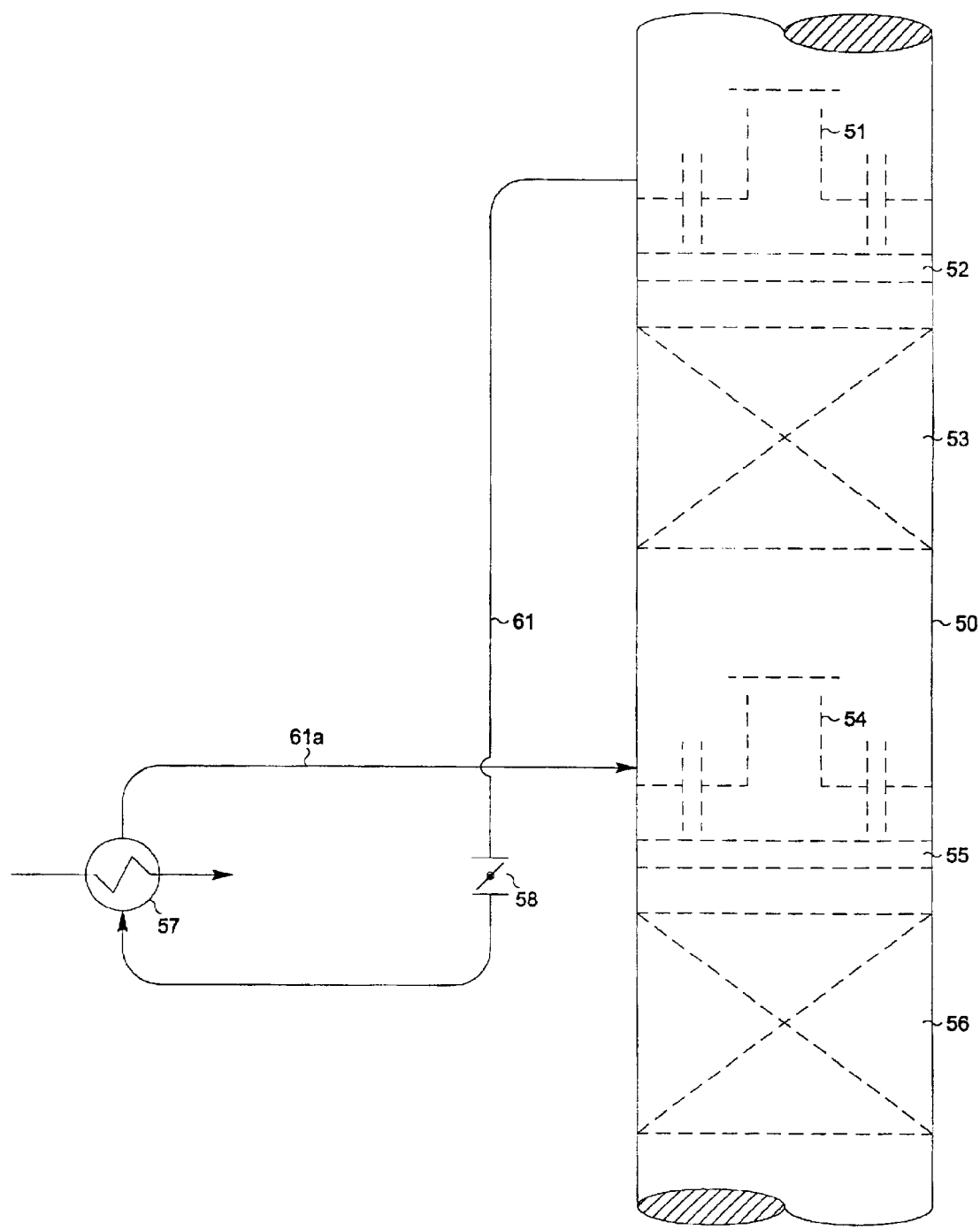
FIG. 6 is a diagram illustrating the modified reboiler scheme of the present invention for a processing plant wherein the scheme includes a thermosiphon system.
Figure 7:
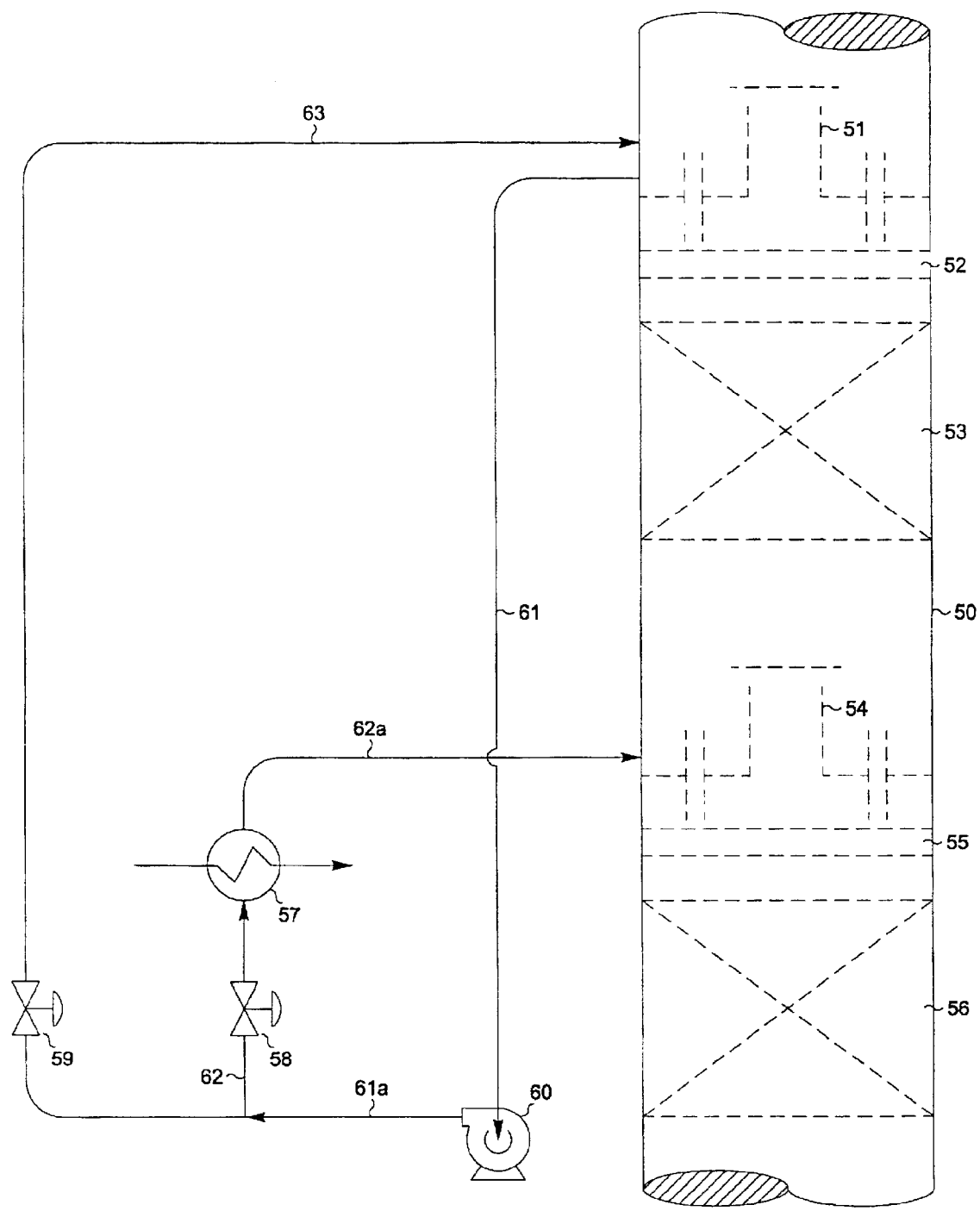
FIG. 7 is a diagram illustrating the modified reboiler scheme of the present invention for a processing plant wherein the scheme includes a pumped system.
Figure 8:
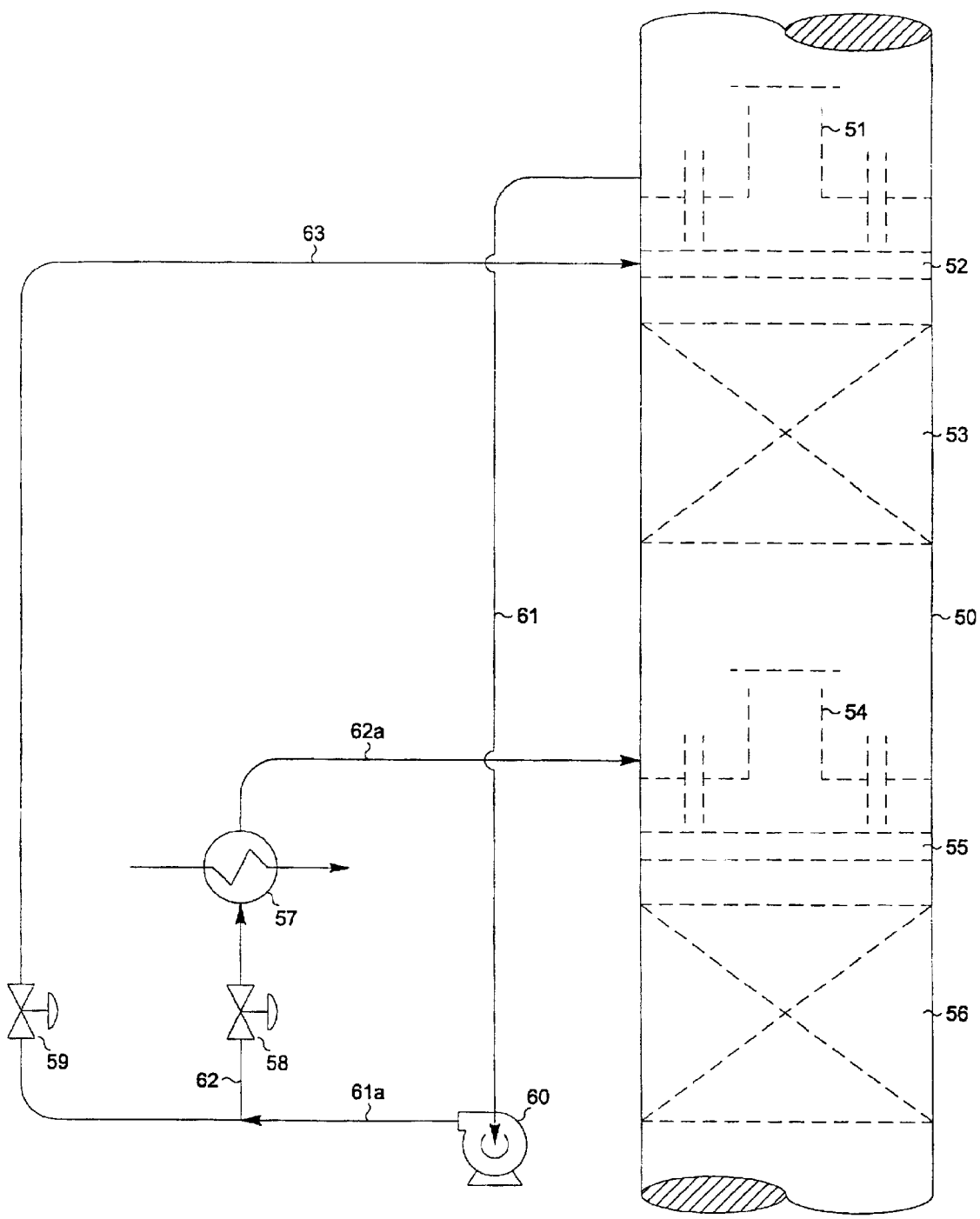
FIG. 8 is a diagram illustrating the modified reboiler scheme of the present invention for a processing plant wherein the scheme includes a pumped system.
Figure 9:
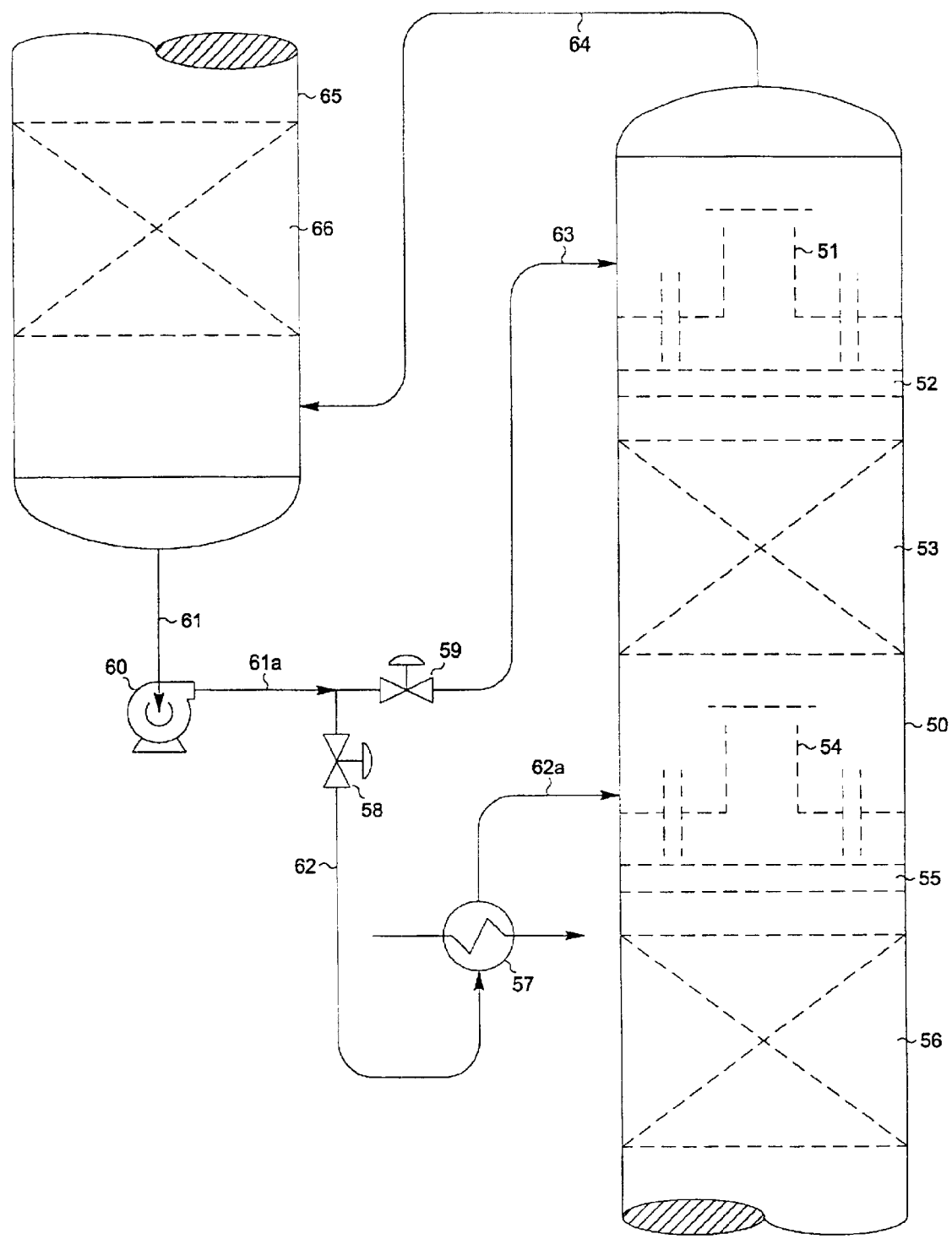
FIG. 9 is a diagram illustrating the modified reboiler scheme of the present invention for a processing plant wherein the scheme includes a split column system.

FIGS. 6, 7, 8, and 9 are diagrams showing some of the alternative methods for implementing the modified reboiler scheme. FIG. 6 shows a typical thermosiphon type application wherein the partial flow of liquid from fractionation tower 50 to reboiler 57 could be controlled via valve 58 in liquid draw line 61. The liquid portion not withdrawn from the column simply overflows chimney tray 51 onto distributor 52 for packing (or trays) 53 below. The heated stream in line 61 *a* from reboiler 57 is returned to fractionation tower 50 at a lower point which contains an appropriate feed distribution mechanism, such as chimney tray 54 and distributor 55, to mix the heated stream with the down-flowing tower liquids from packing (or trays) 53 and supply the mixture to packing (or trays) 56. FIGS. 7 and 8 show typical pumped adaptations wherein the total liquid down-flow is withdrawn in liquid draw line 61 and pumped to higher pressure by pump 60. The flow of the pumped liquid in line 61 a is then divided via appropriate control valves 58 and 59 to arrive at the desired quantity of liquid in line 62 flowing to reboiler 57. The heated stream in line 62*a* from reboiler 57 is returned to fractionation tower 50 at a lower point as described previously for the FIG. 6 embodiment. In the FIG. 7 embodiment, the liquid that does not flow to the reboiler (in line 63) is returned to chimney tray 51 from which the liquid was initially withdrawn, whereupon it can overflow chimney tray 51 onto distributor 52 for packing (or trays) 53 below. In the FIG. 8 embodiment, the liquid that does not flow to the reboiler (in line 63) is returned below chimney tray 51 from which the liquid was initially withdrawn, directly to distributor 52 that supplies the liquid to packing (or trays) 53 below. FIG. 9 shows how the pumped system described for FIG. 8 can be implemented in a split column approach, such as upper column 65 and lower column 50.

One skilled in the art will recognize that the present invention gains some of its benefit by providing a colder stream to the side reboiler(s) and/or reboiler(s), allowing additional cooling of the column feed or feeds. This additional cooling reduces utility requirements for a given product recovery level, or improves product recovery levels for a given utility consumption, or some combination thereof. Further, one skilled in the art will recognize that the present invention also benefits by introducing greater quantities of methane lower in the demethanizer to assist in stripping carbon dioxide from the down-flowing liquids. With more methane available for stripping the liquids, correspondingly less ethane is needed for stripping, allowing more retention of ethane in the bottom liquid product. Therefore, the present invention is generally applicable to any process dependent on cooling any number of feed streams and supplying the resulting feed stream(s) to the column for distillation.

In accordance with this invention, the cooling of the demethanizer feed streams may be accomplished in many ways. In the process of FIGS. 2, 3, and 4, cold residue gas (stream 37) and the demethanizer liquids (streams 40, 42, and 43) are used only for gas stream cooling. In the process of FIG. 5, feed stream 36 is cooled and substantially condensed by cold residue gas (stream 37), distillation column overhead vapor (stream 47) is cooled and partially condensed by expanded stream 36*b*, while the expanded separator liquid (stream 35*a*) and the demethanizer liquid (stream 40) are used only for gas cooling. However, demethanizer liquids could be used to supply some or all of the cooling and substantial condensation of stream 36 in FIG. 5 or the cooling and partial condensation of stream 47 in FIG. 5 in addition to or instead of gas stream cooling. Further, any stream at a temperature colder than the feed stream being cooled may be utilized. For instance, a side draw of vapor from the demethanizer could be withdrawn and used for cooling. Other potential sources of cooling include, but are not limited to, flashed high pressure separator liquids (such as indicated by the dashed line in FIG. 3) and mechanical refrigeration systems. The selection of a source of cooling will depend on a number of factors including, but not limited to, inlet gas composition and conditions, plant size, heat exchanger size, potential cooling source temperature, etc. One skilled in the art will also recognize that any combination of the above cooling sources or methods of cooling may be employed in combination to achieve the desired feed stream temperature(s).

In accordance with this invention, the use of external refrigeration to supplement the cooling available to the inlet gas from other process streams may be employed, particularly in the case of an inlet gas richer than that used in the Example. The use and distribution of demethanizer liquids for process heat exchange, and the particular arrangement of heat exchangers for inlet gas cooling must be evaluated for each particular application, as well as the choice of process streams for specific heat exchange services.

The high pressure liquid in FIG. 5 (stream 35) can be combined with the portion of the separator vapor (stream 33) flowing to heat exchanger 12. Alternatively, this liquid stream (or a portion thereof) may be expanded through an appropriate expansion device, such as expansion valve 16, and fed to a lower mid-column feed point on the distillation column (demethanizer tower 17 in FIG. 5). The liquid stream may also be used for inlet gas cooling or other heat exchange service before or after the expansion step prior to flowing to the demethanizer, as illustrated in FIG. 5.

It will also be recognized that the relative amount of feed found in each branch of the column feed streams will depend on several factors, including gas pressure, feed gas composition, the amount of heat which can economically be extracted from the feed and the quantity of horsepower available. More feed to the top of the column may increase recovery while decreasing power recovered from the expansion machine thereby increasing the recompression horsepower requirements. Increasing feed lower in the column reduces the horsepower consumption but may also reduce product recovery. However, the relative locations of the mid-column feeds may vary depending on inlet composition or other factors such as desired recovery levels and amount of liquid formed during inlet gas cooling. Moreover, two or more of the feed streams, or portions thereof, may be combined depending on the relative temperatures and quantities of individual streams, and the combined stream then fed to a mid-column feed position. FIG. 2 is the preferred embodiment for the compositions and pressure conditions shown. Although individual stream expansion is depicted in particular expansion devices, alternative expansion means may be employed where appropriate. For example, conditions may warrant work expansion of the substantially condensed portion of the feed stream (stream 36a in FIG. 5).

The fractionation towers depicted as single columns in FIGS. 2 through 5 can instead be constructed in two sections (an absorbing section and a stripping section, for instance) because of the size of the plant. The decision whether to construct the fractionation tower as a single vessel (such as tower 17 in FIGS. 2 through 5) or multiple vessels will depend on a number of factors such as plant size, the distance to fabrication facilities, etc.

While there have been described what are believed to be preferred embodiments of the invention, those skilled in the art will recognize that other and further modifications may be made thereto, e.g. to adapt the invention to various conditions, types of feed, or other requirements, without departing from the spirit of the present invention as defined by the following claims.

We claim:

1. In a process for the separation of a gas stream containing methane, $C_2$ components, $C_3$ components and heavier hydrocarbon components into a volatile residue gas fraction containing a major portion of said methane and a relatively less volatile fraction containing a major portion of said $C_2$ components, $C_3$ components and heavier hydrocarbon components, in which process
   (a) said gas stream is treated in one or more heat exchange steps to produce at least a first feed stream that has been cooled under pressure;
   (b) said cooled first feed stream is expanded to a lower pressure, and thereafter supplied to a fractionation tower at a top feed point; and
   (c) said cooled expanded first feed stream is fractionated at said lower pressure whereby the components of said relatively less volatile fraction are recovered;
   the improvement wherein
   (1) a liquid distillation stream is withdrawn from said fractionation tower and heated;
   (2) said heated distillation stream is returned to a lower point on said fractionation tower that is separated from said withdrawal point by at least one theoretical stage; and
   (3) the quantities and temperatures of said feed streams to said fractionation tower are effective to maintain the overhead temperature of said fractionation tower at a temperature whereby the major portions of the components in said relatively less volatile fraction are recovered.

2. In a process for the separation of a gas stream containing methane, $C_2$ components, $C_3$ components and heavier hydrocarbon components into a volatile residue gas fraction containing a major portion of said methane and a relatively less volatile fraction containing a major portion of said $C_2$ components, $C_3$ components and heavier hydrocarbon components, in which process
   (a) said gas stream is treated in one or more heat exchange steps and at least one division step to produce at least a first feed stream that has been cooled under pressure to condense substantially all of it, and at least a second feed stream that has been cooled under pressure;
   (b) said substantially condensed first feed stream is expanded to a lower pressure whereby it is further cooled, and thereafter directed in heat exchanger relation with a warmer distillation stream which rises from fractionation stages of a fractionation tower;
   (c) said distillation stream is cooled by said first stream sufficiently to partially condense it, whereupon said partially condensed distillation stream is separated to provide said volatile residue gas fraction and a reflux stream, with said reflux stream thereafter supplied to said fractionation tower at a top feed point;
   (d) said warmed first stream is supplied to said fractionation tower at a first mid-column feed point;
   (e) said cooled second feed stream is expanded to said lower pressure, and thereafter supplied to said fractionation tower at a second mid-column feed point; and
   (f) said reflux stream, said heated first feed stream, and said expanded second feed stream are fractionated at said lower pressure whereby the components of said relatively less volatile fraction are recovered;
   the improvement wherein (1) a liquid distillation stream is withdrawn from said fractionation tower and heated;

(2) said heated distillation stream is returned to a lower point on said fractionation tower that is separated from said withdrawal point by at least one theoretical stage; and (3) the quantities and temperatures of said feed streams to said fractionation tower are effective to maintain the overhead temperature of said fractionation tower at a temperature whereby the major portions of the components in said relatively less volatile fraction are recovered.

3. The improvement according to claims 1 or 2 wherein said liquid distillation stream is pumped after being withdrawn from said fractionation tower.

4. The improvement according to claim 3 wherein
(a) said pumped liquid distillation stream is divided into at least a first portion and a second portion;
(b) said first portion is heated; and
(c) said heated first portion is returned to a lower point on said fractionation tower that is separated from said withdrawal point by at least one theoretical stage.

5. The improvement according to claims 1 or 2 wherein said liquid distillation stream is directed in heat exchange relation with at least a portion of said gas stream or said feed streams, to supply said cooling thereto and thereby heat said liquid distillation stream.

6. The improvement according to claim 3 wherein said pumped liquid distillation stream is directed in heat exchange relation with at least a portion of said gas stream or said feed streams, to supply said cooling thereto and thereby heat said pumped liquid distillation stream.

7. The improvement according to claim 4 wherein said first portion is directed in heat exchange relation with at least a portion of said gas stream or said feed streams, to supply said cooling thereto and thereby heat said first portion.

8. The improvement according to claims 1 or 2 wherein the quantity and temperature of said heated distillation stream and the heating supplied to said fractionation tower are effective to maintain the bottom temperature of said fractionation tower at a temperature to reduce the quantity of carbon dioxide contained in said relatively less volatile fraction.

9. The improvement according to claim 3 wherein the quantity and temperature of said heated distillation stream and the heating supplied to said fractionation tower are effective to maintain the bottom temperature of said fractionation tower at a temperature to reduce the quantity of carbon dioxide contained in said relatively less volatile fraction.

10. The improvement according to claim 4 wherein the quantity and temperature of said heated first portion and the heating supplied to said fractionation tower are effective to maintain the bottom temperature of said fractionation tower at a temperature to reduce the quantity of carbon dioxide contained in said relatively less volatile fraction.

11. The improvement according to claim 5 wherein the quantity and temperature of said heated distillation stream and the heating supplied to said fractionation tower are effective to maintain the bottom temperature of said fractionation tower at a temperature to reduce the quantity of carbon dioxide contained in said relatively less volatile fraction.

12. The improvement according to claim 6 wherein the quantity and temperature of said heated distillation stream and the heating supplied to said fractionation tower are effective to maintain the bottom temperature of said fractionation tower at a temperature to reduce the quantity of carbon dioxide contained in said relatively less volatile fraction.

13. The improvement according to claim 7 wherein the quantity and temperature of said heated first portion and the heating supplied to said fractionation tower are effective to maintain the bottom temperature of said fractionation tower at a temperature to reduce the quantity of carbon dioxide contained in said relatively less volatile fraction.

* * * * *